US00PP19627P3

(12) United States Plant Patent
VanLaeken

(10) Patent No.: US PP19,627 P3
(45) Date of Patent: Jan. 20, 2009

(54) ***CLEMATIS* PLANT NAMED 'AMERICAN BEAUTY'**

(50) Latin Name: ***Clematis* sp.**
Varietal Denomination: American Beauty

(76) Inventor: James P. VanLaeken, 3242 Daansen Rd., Walworth, NY (US) 14568

( * ) Notice: Subject to any disclaimer, the term of this patent is extended or adjusted under 35 U.S.C. 154(b) by 121 days.

(21) Appl. No.: 11/706,164

(22) Filed: Feb. 15, 2007

(65) Prior Publication Data

US 2008/0201810 P1 Aug. 21, 2008

(51) Int. Cl.
*A01H 5/00* (2006.01)

(52) U.S. Cl. ..... Plt./228

(58) Field of Classification Search ..... Plt./228
See application file for complete search history.

(56) References Cited

PUBLICATIONS

Spring Valley Greenhouse, Inc. Catalog (6th addition p. #3 Etoile de Malicorne).

*Primary Examiner*—Kent L Bell

(57) ABSTRACT

A new variety of *clematis* plant named 'American Beauty'. The variety is characterized by it's unique color combination of red, white and blue.

2 Drawing Sheets

Botanical classification: *Clematis* sp.
Cultivar designation: 'American Beauty'.

BACKGROUND OF THE VARIETY

The present invention relates to a new and distinct variety of hybrid *clematis* plant known by the cultivar name 'American Beauty'.

The new variety was a seedling found growing in a controlled planting of *clematis* display garden at a *clematis* nursery in Walworth, N.Y. in 2002. Plants were asexually propagated and observed over the next four years. Asexual propagation by vegetative cuttings has shown that the propagules are identical to the original plant in all distinguished characteristics. The stability of the variety is evidenced by the distinguished characteristics remaining true to form from generation to generation. The parentage of the variety is unknown.

SUMMARY OF THE INVENTION

Among the features which distinguish the new variety from other present available and known commercial *clematis* cultivars are the unique color of the flower, plus its long blooming period. The flower has violet tepals with darker red bar fading at tepal point. The unique three color variations going from red, white and blue.

RELEVANT PRIOR ART

The new variety is some what similar in appearance to *Clematis* sp. 'Etiole de Malicorne' variety as shown in Spring Valley, Inc. ($6^{th}$ Edition) on page 3. Both flowers are similar in that they both have 6 tepals. The tepals are broader on 'American Beauty' and the bar is brighter and more vivid. 'American Beauty' has a more compact growth habit that is ideal for containers. The time of bloom is similar but 'American Beauty' has more flowers per stem.

BRIEF DISCRITION OF THE PHOTOGRAPH

The accompanying photograph illustrates the overall appearance of the new variety. The flowering and foliage colors as shown are, within the limitations of color photography, accurate and true reproductions of the actual colors of new variety.

The photographic view is a front elevation of typical *Clematis* sp. 'American Beauty'.

We are also including a photograph showing flower bud formations, showing the profuse blooming nature of the plant.

BOTANICAL DISCRIPTION

The following information is based on a three year old plant grown in 50% shade in a five gallon container in a covered greenhouse with 60° F. ambient night temperatures and 75° F. ambient day temperatures in Walworth, N.Y. Color references are based on using the PANTONE® matching system.

1. Plant:
   - *A. Form.*—Uright climbing or spreading.
   - *B. Growth.*—Vigorous, vining. 1. Height: approximately 4 feet to 6 feet. 2. Diameter/Spread: approximately 2 feet to 3 feet.
   - *C. Foliage.*—Deciduous, compound-trifoliate, opposite. 1. Size, typical and observed: a. compound leaf length 5 inches, width 4 inches. b. individual leaflets length 2.5 to 3.5 inches, width 1 to 2 inches. c. leaflets per compound leaf: 3. 2. Quantity of leaves per stem: typically and observed: about 28. 3. Color a. upper surface: dark green (PANTONE® #575U). b. lower surface: medium green (PANTONE® #576U). 4. Shape a. leaflets: base is rounded, margin is untoothed with glabrous edge, apex is pointed. 5. Texture a. upperside: smooth and veined. b. underside: ribbed and glabrous. c. veination pattern: leaflets palmatic with green coloration on upper and lower. 6. Petiole a. color: reddish brown (PANTONE® #483U). b. length, typical and observed: 1 to 3 inches. c. diameter, typical and observed: ⅛ inch. d. glabrous: yes.

*D. Wood.— 1.* New Shoots a. color: medium green (PANTONE® #576C). b. bark: smooth and glabrous. c. internodes: cylindrical, approximately 4 to 5 inches in length and ⅛ inch in diameter. 2. Old Wood a. color: medium brown (PANTONE® #463C). b. bark: smooth ⅛ inch in diameter and glabrous. c. internodes: cylindrical, approximately 4 to 5 inches in length and ⅛ inch in diameter and glabrous.

*E. Hardiness.*—US Zones 4 through 8. 1. low temperature tolerance, typical and observed: −10° F. to 0° F. 2. high temperature tolerance, typical and observed: 90° F. to 110° F.; requires 6 to 8 weeks dormancy at 35° F. to 40° F. to remain vigorous.

*F. Disease.*— 1. subject to any disease that affects *clematis*. b. wilt. c. botrytis. d. powdery mildew.

*G. Pests.*— 1. subject to any pest that normally affect *clematis*. a. aphids. b. spider mites. e. slugs and snails.

II. Flower:

*A. Blooming habit.*—May through October based on climate in Rochester, New York area.

*B. Bud.*— 1. Size: typical and observed from about 2 to 3 inches in length and about ½ to 1 inch in diameter. 2. Form: ovate base with pointed tip and glabrous. 3. Color: light green with white veins (PANTONE® #584U).

*C. Stem.*— 1. Dimension, typical and observed: length 0.5 to 2 inches, diameter 1/16 inch. 2. Aspect: vertical. 3. strength: erect. 4. Color: green (PANTONE® #377C).

*D. Bloom.*— 1. Size: typical and observed from about 5 to 7 inches in diameter with a depth of about 1 inch. 2. Form: round cross shaped with 4 to 5 tepals of equal size seldom overlapping. 3. Color upper surface: violet red (PANTONE® #2577C) with reddish bar (PANTONE® #232C). 4. Color of lower surface: edges bluish purple (PANTONE® #266C) with heavy veined whitish mid rib. 5. Characteristics: born on 0.5 to 2 inch stems on new growth. 6. Quantity: 1 bloom per stem, 3 buds per node, 3 to 100 blooms per plant depending on the age and size of plant. 7. lastingness: 3 to 6 days as a cut flower or 10 to 14 days on plant.

*E. Tepals.*— 1. Form: irregular in shape starting with a wide wedge shaped ½ inch base expanding half way up to 1.5 inches at widest point and then tapering down to a pointed apex. Tepal edges curve downward. The overall tepal length being 2.5 to 3.5 inches with irregular toothed edges. 2. Arrangement of tepals: regularly arranged seldom overlapping. 3. Fragrance: none. 4. Color: (see II D 3 and II D 4 above).

III. Reproductive organs:

*A. Stamens, filaments and anthers.*— 1. Arrangement: regularly arranged. 2. Stamens: typical and observed 40 to 45 per bioom, length ¾ inch. 3. Anthers: length ¼ inch (PANTONE® #195U) reddish/brown. 4. Filament: white.

*B. Pollen.*— 1. Color: white. 2. Amount: scarce.

*C. Styles.*—Bunched, even, average length (PANTONE® #195U) reddish/brown.

*D. Stigmas.*— 1. Color: white.

*E. Seed,typical and observed.*— 1. Diameter: 1/16 inch. 2. Thickness: 1.32 inch. 3. Color: (PANTONE® #383C) yellowish/green. 4. Shape: oval. 5. Quantity per bloom: 30 to 35. 6. Description: ¾ inch long persistent style which is clothed with silky white hairs.

I claim:

1. A new and distinct variety of *clematis* plant named 'American Beauty' as shown and described herein.

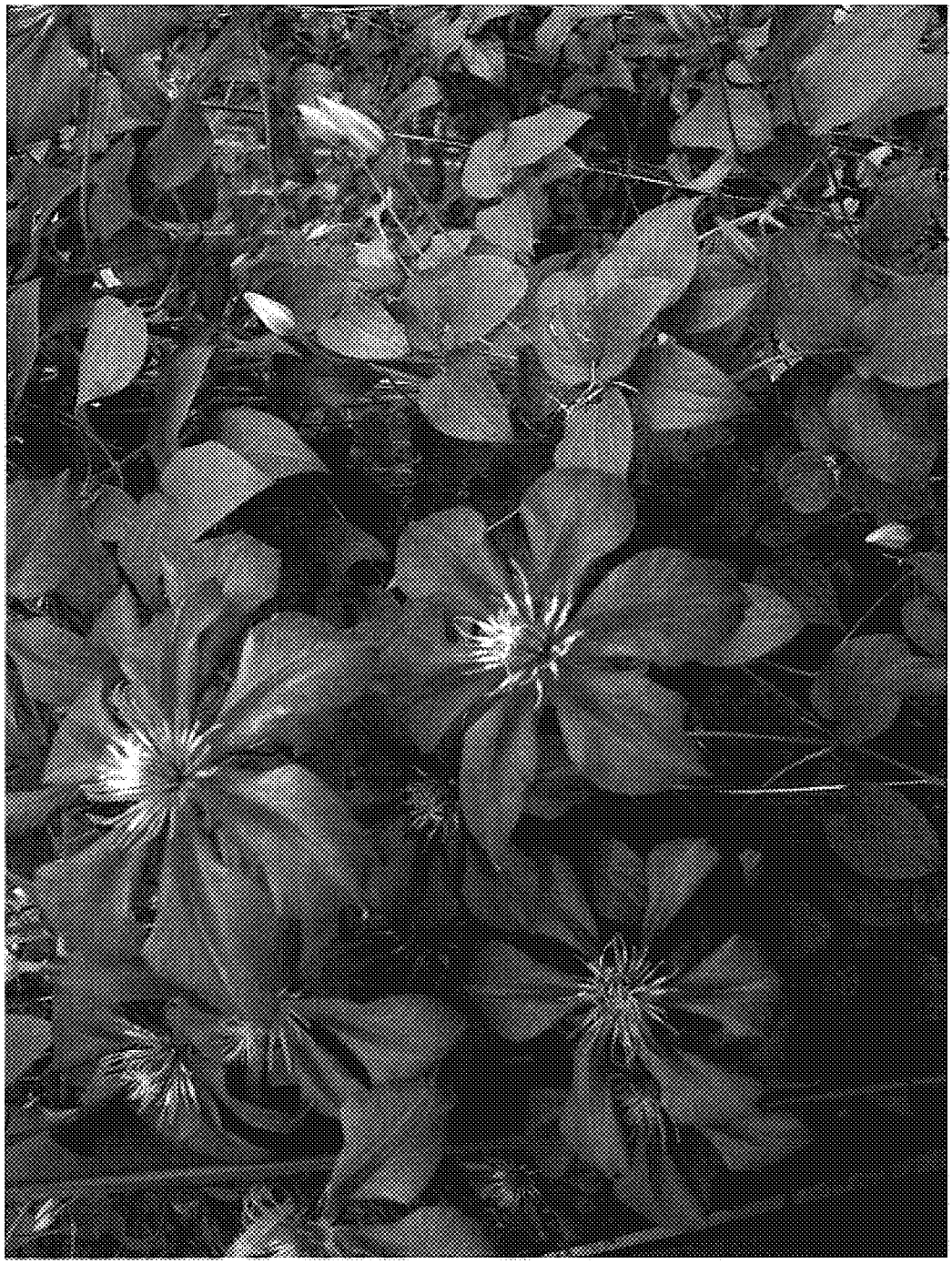

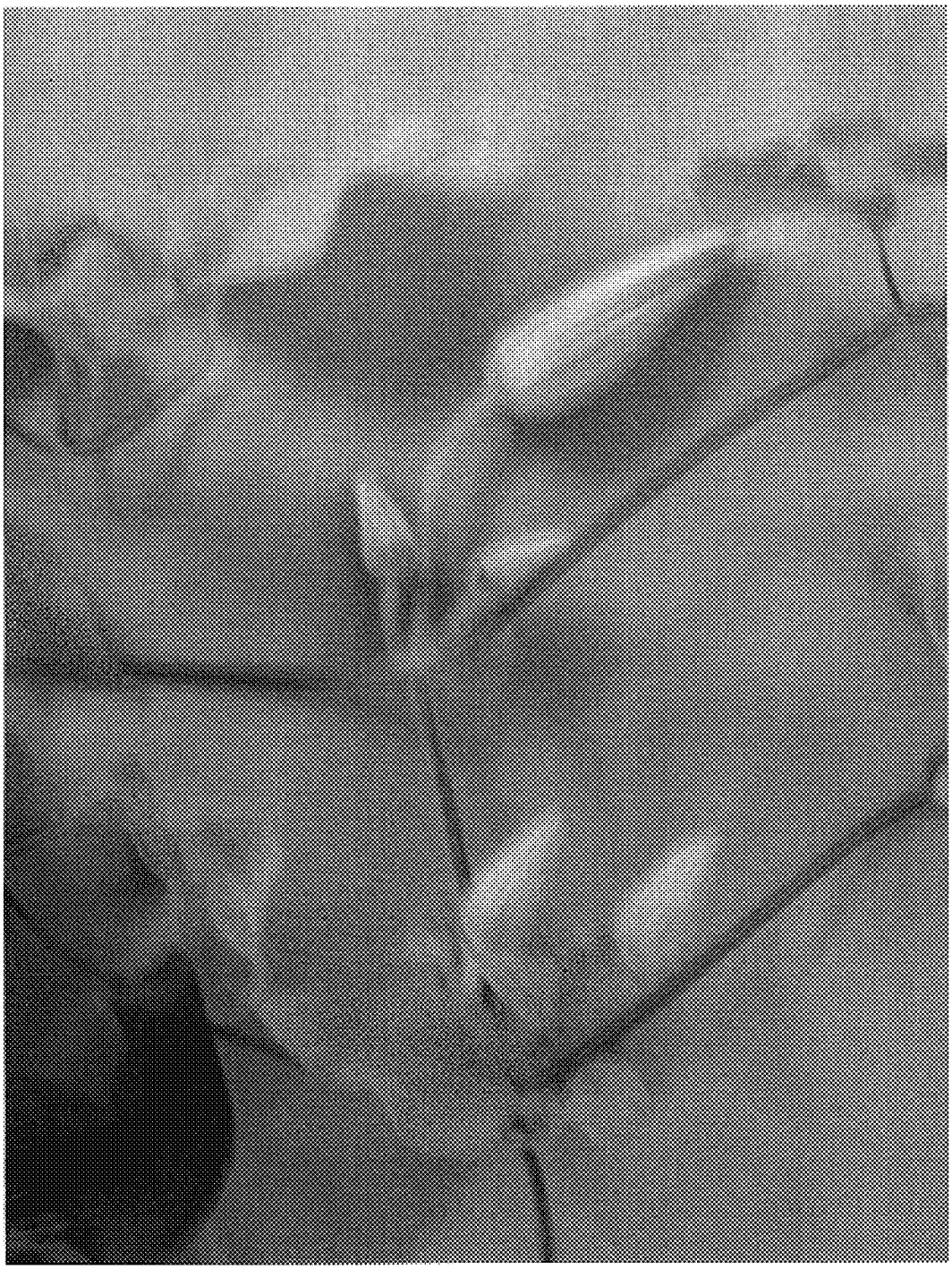

* * * * *